United States Patent
Kawabata et al.

[11] Patent Number: 6,022,496
[45] Date of Patent: Feb. 8, 2000

[54] CHROMENE COMPOUND

[75] Inventors: Yuichiro Kawabata; Tsuneyoshi Tanizawa; Tadashi Hara, all of Tokuyama, Japan

[73] Assignee: Tokuyama Corporation, Yamaguchi-ken, Japan

[21] Appl. No.: 09/253,544

[22] Filed: Feb. 22, 1999

Related U.S. Application Data

[62] Division of application No. 09/070,018, Apr. 30, 1998, Pat. No. 5,932,725.

[30] Foreign Application Priority Data

Apr. 30, 1997 [JP] Japan ................................ 9-112972

[51] Int. Cl.$^7$ .................... G02B 5/23; G02C 7/10
[52] U.S. Cl. ............................ 252/586; 351/163
[58] Field of Search ................... 252/586; 549/389; 544/60, 62, 375, 376; 546/112, 164, 269; 548/454, 511; 351/163, 44

[56] References Cited

U.S. PATENT DOCUMENTS

| | | |
|---|---|---|
| 3,567,605 | 3/1971 | Becker . |
| 5,552,090 | 9/1996 | Van Gemert et al. .................. 252/586 |
| 5,623,005 | 4/1997 | Rickwood et al. ...................... 252/586 |

FOREIGN PATENT DOCUMENTS 9422850  10/1994  WIPO .

*Primary Examiner*—Philip Tucker

[57] ABSTRACT

The present invention relates to a novel chromene compound having favorable photochromic properties, developing a color of a high density, exhibiting a small degree of initial color and permitting the color to quickly fade. The novel chromene compound has an amino group that may be substituted for a sixth position of a naphthopiran ring, has electron-donating groups at para-positions of the two phenyl groups bonded to the third position, and has at least one or more electron-attracting groups at meta-positions of the phenyl groups, and is represented, for example, by the following formula,

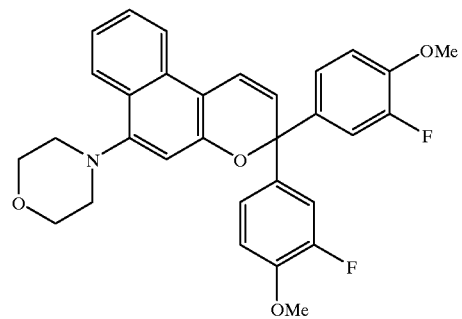

17 Claims, 1 Drawing Sheet

CHROMENE COMPOUND

This application is a division of Ser. No. 09/070,018 filed Apr. 30, 1998 now U.S. Pat. No. 5,932,725.

BACKGROUND OF THE INVENTION

1. Field of the Invention

The present invention relates to a novel chromene compound which changes into a colored state upon irradiation with light containing ultraviolet rays such as of sunlight or light of a mercury lamp, the change being reversible, and exhibits excellent durability.

2. Prior Art

Photochromism is a phenomenon which is drawing attention in these several years, and stands for a reversible action of a compound; i.e., a compound quickly changes its color when it is irradiated with light containing ultraviolet rays such as of sunlight or light of a mercury lamp, and resumes its initial color when it is no longer irradiated with light and is placed in a dark place. The compound having such a property is called photochromic compound. Though a variety of compounds have heretofore been synthesized, no common feature is particularly recognized among their structures.

U.S. Pat. No. 3,567,605 discloses a chromene compound represented by the following formula,

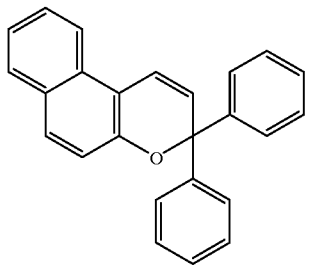

This chromene compound exhibits photochromic property near room temperature (20 to 30° C.) but develops a color of only a low density upon the irradiation with ultraviolet rays, and is not practicable.

Furthermore, WO9422850 discloses a chromene compound represented by the following formula,

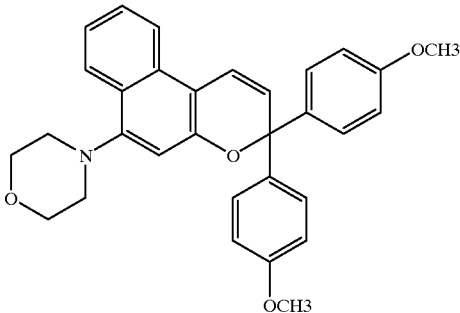

This compound develops a color of a higher density than the compound disclosed in the above-mentioned U.S. Pat. No. 3,567,605. However, when dispersed in a solvent or a matrix, the compound partly develops a color, i.e., initially colored to a large extent and is not practicable.

SUMMARY OF THE INVENTION

The object of the present invention therefore is to provide a chromene compound which develops a color at a density sufficiently higher than that of the above-mentioned compound, which is initially colored little, and which permits the color to fade quickly.

The present invention was proposed in order to accomplish the above-mentioned object, and was finished based on a discovery that a novel chromene compound of the invention develops color of a high density, is initially colored little, and permits the color to fade quickly.

That is, the present invention is concerned with a chromene compound represented by the following general formula (1),

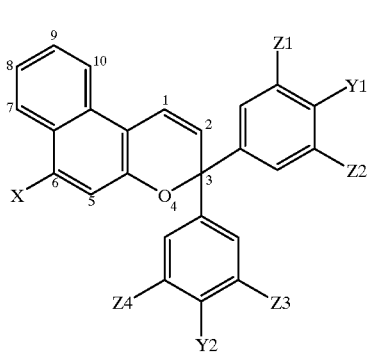

(1)

wherein X is an amino group represented by the following formula (2),

(2)

wherein R1 and R2 may be the same or different, and are hydrogen atoms, substituted or unsubstituted alkyl groups having 1 to 10 carbon atoms, substituted or unsubstituted aryl groups or hetero rings, having 6 to 10 carbon atoms, or a cyclic amino group represented by the following formula (3),

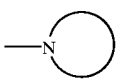

(3)

wherein the ring may contain a hetero atom, or may contain a hetero ring and/or aromatic ring in a condensed form, Y1 and Y2 may be the same or different and are electron-donating groups, Z1, Z2, Z3 and Z4 may be the same or different and are hydrogen atoms or electron-attracting groups, at least one of Z1 to Z4 is an electron-attracting group, and a carbon atom at any one of fifth position, seventh position, eighth position, ninth position or tenth position of a naphthopyran ring may have a substituent.

The invention is further concerned with a photochromic material comprising a chromene compound represented by the above-mentioned general formula (1), and with photochromic lens containing a chromene compound represented by the above-mentioned general formula (1).

DETAILED DESCRIPTION OF THE PREFERRED EMBODIMENTS

Figure 1:
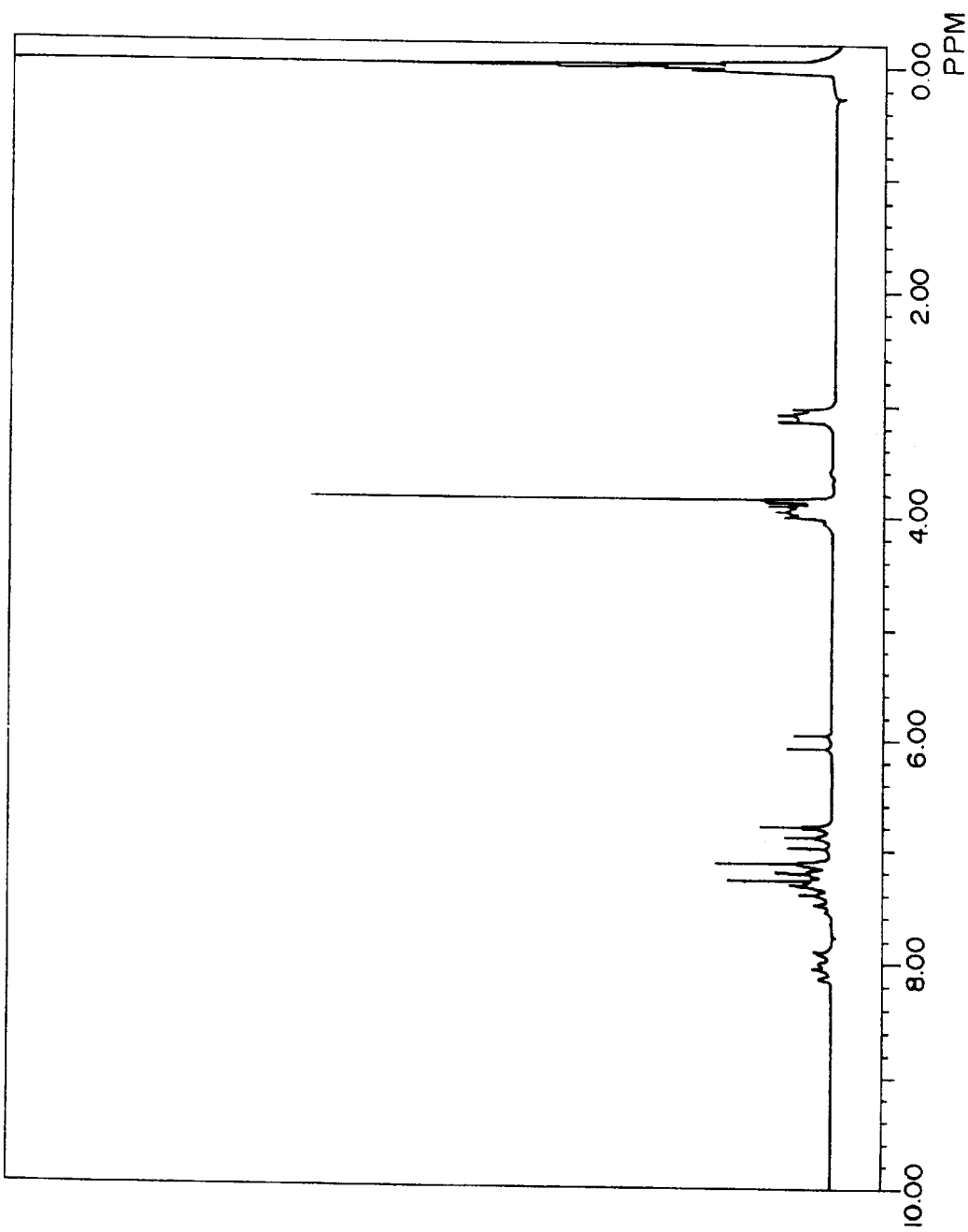
FIG. 1 is a diagram of a proton nuclear magnetic resonance spectrum of a compound of Example 1.

In the above-mentioned general formula (1), the group X present at the sixth position of the chromene ring is an amino group represented by the following formula (2),

(2)

wherein R1 and R2 may be the same or different and are hydrogen atoms, substituted or unsubstituted alkyl groups having 1 to 10 carbon atoms, substituted or unsubstituted aryl groups or hetero rings, having 6 to 10 carbon atoms, or is an amino group represented by the following formula (3),

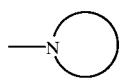

(3)

wherein the ring may contain a hetero atom, or may contain a hetero ring and/or an aromatic ring in a condensed form.

Any known group can be used without limitation as the substituted or unsubstituted alkyl group having 1 to 10 carbon atoms, as the substituted or unsubstituted aryl group having 6 to 10 carbon atoms, or as the hetero ring represented by R1 and R2 in the above-mentioned formula (2). It is, however, preferred to use an alkyl group having 1 to 4 carbon atoms, a phenyl group or a naphthyl group.

Concrete examples of the substituted amino group in the above-mentioned formula (2) include methylamino group, ethylamino group, propylamino group, isopropylamino group, dimethylamino group, diethylamino group, dipropylamino group, methylethylamino group, 2-hydroxyethylamino group, di(2-hydroxyethyl)amino group, di(cyanomethyl)amino group, diphenylamino group and the like group.

In the cyclic amino group represented by the above-mentioned formula (3), there is no particular limitation on the number of carbon atoms constituting the cyclic amino group. Preferably, however, the number of carbon atoms is from 2 to 10 and, more preferably, from 3 to 6. Though there is no particular limitation on the hetero atom that may exist in the ring of the cyclic amino group, it is desired to use an oxygen atom, a sulfur atom or a nitrogen atom. Moreover, though there is no particular limitation on the hetero ring or on the aromatic ring that may be condensed in the ring, it is desired to use a hetero ring and an aromatic ring having 6 to 10 carbon atoms. Preferred examples of the hetero ring and aromatic ring include benzene ring, naphthalene ring, (tetrahydro)thiophene ring, and (tetrahydro)furan ring.

Concrete examples of the cyclic amino group represented by the above-mentioned formula (3) include pyrrolidinyl group, piperidino group, 2,2,6,6-tetramethylpiperidino group, morpholino group, 2,6-dimethylmorpholino group, N-methylpiperazinyl group, thiomorpholino group, indolinyl group, methyl indolinyl group, tetrahydroquinolyl group, aziridinyl group and the like group.

When the amino group represented by the above-mentioned mentioned general formula (2) is compared with the cyclic amino group represented by the general formula (3), the cyclic amino group represented by the general formula (3) is preferred to the amino group represented by the general formula (2) since it is initially colored to a small degree.

In the above-mentioned general formula (1), the substituents Y1 and Y2 of the phenyl group bonded to the third position of the naphthopyrane ring are electron-donating groups which may be different from each other, and Z1, Z2, Z3 and Z4 are hydrogen atoms or electron-attracting groups which may be different from each other, and at least one of Z1 to Z4 is an electron-attracting group.

Upon introducing the electron-donating group into the para-position of the phenyl group and upon making at least one or more electron-attracting groups present at the meta-positions, the chromene compound represented by the above-mentioned general formula (1) becomes initially colored to a small degree and permits the color to fade quickly. When no electron-attracting group exists at the meta-position, on the other hand, the chromene compound is initially colored to a large degree. When the electron-attracting group is introduced at the ortho-position or at the para-position of the phenyl group, the chromene compound permits the color to fade slowly. Therefore, none of them are practicable.

Any electron-donating group can be used without limitation as Y1 and Y2 in the above-mentioned general formula (1). Preferred examples include alkyl group, alkoxyl group, alkoxyalkyl group, aralkyl group, substituted amino group, aryloxyl group, acyloxyl group and, more preferably, alkyl group, alkoxy group, alkoxyalkyl group and aryloxyl group.

Upon introducing these preferred electron-donating substituents, the rate for fading the color can be quickened effectively.

Preferred electron-donating groups will now be described.

Though there is no particular limitation, the alkyl group generally has 1 to 10 carbon atoms and, preferably, 1 to 4 carbon atoms. Concrete examples of the alkyl group include methyl group, ethyl group, n-propyl group, isopropyl group, n-butyl group, and t-butyl group.

Though there is no particular limitation, the alkoxyl group generally has 1 to 10 carbon atoms and, preferably, 1 to 4 carbon atoms. Concrete examples of the alkoxyl group include methoxy group, ethoxy group, n-propoxy group, isopropoxy group, n-butoxy group, t-butoxy group and methoxyethoxy group.

Though there is no particular limitation, the alkoxyalkyl group generally has 2 to 10 carbon atoms and, preferably, 2 to 6 carbon atoms. Concrete examples of the alkoxyalkyl group include methoxymethyl group, ethoxymethyl group, propoxymethyl group, dimethoxymethyl group, 2,5-dioxacyclopentane-1-yl group, butoxymethyl group, methoxyethyl group and ethoxyethyl group.

Though there is no particular limitation, the aralkyl group generally has 7 to 16 carbon atoms and, preferably, 7 to 10 carbon atoms. Concrete examples of the aralkyl group include benzyl group, phenylethyl group, phenylpropyl group and phenylbutyl group.

Though there is no particular limitation, the acyloxyl group generally has 1 to 15 carbon atoms and, preferably, 1 to 6 carbon atoms. Concrete examples of the acyloxyl group include acetoxyl group, propionyloxyl group, butyryloxyl group, benzoyloxyl group and (meta)acryloyloxyl group.

Though there is no particular limitation, the substituted amino group generally has a substituent such as an alkyl group with 1 to 10 carbon atoms or a hetero atom-containing alkyl group. The substituted amino group may form a ring.

Concrete examples of the substituted amino group include methylamino group, ethylamino group, propylamino group, isopropylamino group, dimethylamino group, diethylamino group, dipropylamino group, methylethylamino group, 2-hydroxyethylamino group, di(2-hydroxyethyl)amino group, piperidino group, morpholino group, N-methylpiperadinyl group, thiomorpholino group, aziridinyl group, indolinyl group, and tetrahydroquinolinyl group.

In the above-mentioned general formula (1), it is essential that Z1, Z2, Z3 and Z4 are hydrogen atoms or electron-attracting groups, and at least one of Z1 to Z4 is an electron-attracting group. However, an increase in the number of the electron-attracting groups may decrease the rate for fading the color. It is therefore desired that one to three and, particularly, one to two of Z1 to Z4 are electron-attracting groups. Any electron-attracting group can be used without any particular limitation provided it attracts electrons. Preferred examples include halogen atom, alkoxycarbonyl group, acyl group, cyano group, nitro group, trifluoromethyl group and, more preferably, halogen atom, alkoxycarbonyl group, cyano group and trifluoromethyl group.

Upon introducing these preferred electron-attracting groups, the property for initially developing color can be effectively suppressed.

Preferred electron-attracting groups will be described below.

Though there is no particular limitation on the halogen atoms, concrete examples of the halogen atom that can be preferably used in the present invention include fluorine atom, chlorine atom and bromine atom.

Though there is no particular limitation, the alkoxycarbonyl group generally has 1 to 10 carbon atoms and, preferably, 1 to 7 carbon atoms. Concrete examples of the alkoxycarbonyl group include methoxycarbonyl group, ethoxycarbonyl group, propoxycarbonyl group and butoxycarbonyl group.

Though there is no particular limitation, the acyl group generally has 1 to 15 carbon atoms and, preferably, 1 to 7 carbon atoms. Concrete examples of the acyl group include formyl group, acetyl group, propionyl group, butyryl group and benzoyl group.

Any carbon at the fifth position, seventh position, eighth position, ninth position or tenth position of the naphthopyran ring in the general formula (1) may have a substituent. The effect of the present invention stems from the basic structure (skeleton) represented by the above-mentioned general formula (1); i.e., the effect of the present invention in that the chromene compound is initially colored to a small degree and permits the color to quickly fade, is obtained irrespective of the substituents introduced into the above-mentioned positions of the naphthopyran ring in the skeleton. There is no particular limitation on the substituents that may be introduced into the above-mentioned positions of the naphthopyran ring provided they do not adversely affect the present invention. Preferred examples of the substituents include alkyl group, alkoxyl group, aralkyl group, acyl group, alkoxycarbonyl group, substituted amino group, acyloxyl group, nitro group, hydroxyl group, cyano group and halogen atom. Concrete examples of these substituents will be those exemplified by the above-mentioned mentioned substituents Y1 to Y2 and Z1 to Z4. There is no particular limitation on the positions and on the total number of these substituents provided they are bonded to the fifth position, seventh position, eighth position, ninth position or tenth position of the naphthopyrane ring. Generally, however, the total number of the substituents present at these positions is not larger than 3 and, preferably, not larger than 2.

Preferred combinations of the substituents in the above-mentioned general formula (1) are tabulated below.

TABLE 1

| No. | X | Y1 and Y2 | Z1~Z4 |
|---|---|---|---|
| 1 | amino group of formula (2) in which R1 and R2 are alkyl groups having 1 to 4 carbon atoms, phenyl groups or naphthyl groups or cyclic amino group of formula (3) in which a ring portion has 3 to 6 carbon atoms, and may have a hetero atom or may have a hetero ring or an aromatic ring in a condensed form. | alkyl group, alkoxyl group, alkoxyalkyl grup, aralkyl group, substituted amino group, aryloxyl group or acyloxyl group (Y1 and Y2 may be different from each other). | at least one of Z1 to Z4: at least one group selected from the group consisting of halogen atom, alkoxycarbonyl group, acyl group, cyano group, nitro group and trifluoromethyl group (which may be different from each other). remainder: hydrogen atom |
| 2 | cyclic amino group of No. 1 above (but hetero atom is O, S or N). | Y1: alkoxyl group Y2: alkoxyl group, aryloxyl group or acyloxyl group | at least one of Z1 to Z4: halogen atom, alkoxycarbonyl group, acyl group, cyano group, nitro group or trifluoromethyl group (which may be different from each other). remainder: hydrogen atom |
| 3 | same as above | same as above | one of Z1 to Z4: cyano group, nitro group or trifluoromethyl group. at least two of the remainder: hydrogen atoms remainder: halogen atom, alkoxycarbonyl group or acyl group. |
| 4 | same as above | same as above | two of Z1 to Z4: hydrogen atoms remainder: halogen atom, alkoxycarbonyl group or acyl group (which may be different from each other). |

TABLE 1-continued

| No. | X | Y1 and Y2 | Z1~Z4 |
|---|---|---|---|
| 5 | same as above | Y1: alkoxyl group<br>Y2: alkoxyl group | same as above |
| 6 | same as above | Y1: alkoxyl group<br>Y2: alkoxyl group | one of Z1 to Z4: hydrogen atom<br>remainder: halogen atom or alkoxycarbonyl group |
| 7 | same as above | same as above | same as No. 3 |
| 8 | same as above | Y1: alkoxyl group<br>Y2: alkyl group, alkoxyalkyl group or aralkyl group | at least two of Z1 to Z4: halogen atom, alkoxycarbonyl group, acyl group, cyano group, nitro group or trifluoromethyl group (which may be different from each other).<br>remainder: hydrogen atom |
| 9 | same as above | same as above | at least two of Z1 to Z4: halogen atom, alkoxycarbonyl group, acyl group (which may be different from each other).<br>remainder: hydrogen atom. |
| 10 | same as above | same as above | same as No. 3 |
| 11 | same as above | Y1: alkoxyl group<br>Y2: alkyl group or alkoxyalkyl group | at least two of Z1 to Z4: halogen atom or alkoxycarbonyl group (which may be different from each other).<br>remainder: hydrogen atom |

Concrete examples of the chromene compound that can be favorably used in the present invention include:

1) 3,3-bis(3-fluoro-4-methoxyphenyl)-6-morpholino-3H-benzo (f) chromene;
2) 3-(3,5-difluoro-4-methoxyphenyl)-3-(4-methoxyphenyl)-6-morpholino-3H-benzo (f) chromene;
3) 3,3-bis(3-fluoro-4-methoxyphenyl)-6-(2-methylindolinyl)-3H-benzo (f) chromene;
4) 3-(3-fluoro-4-methoxyphenyl)-3-(4-methoxymethylphenyl)-6-(tetrahydroquinolinyl)-3H-benzo (f) chromene;
5) 3-(3-chloro-4-methylphenyl)-3-(4-methoxyphenyl)-6-(tetrahydroquinolinyl)-3H-benzo (f) chromene;
6) 3-(3-chloro-4-(2-methoxyethoxy)phenyl)-3-(3-fluoro-4-methoxyphenyl)-6-morpholino-3H-benzo (f) chromene;
7) 3-(3-bromo-4-methoxyphenyl)-3-(3-chloro-4-methoxyphenyl)-6-thiomorpholino-3H-benzo (f) chromene;
8) 3-(4-t-butoxyphenyl)-3-(3-trifluoromethyl-4-methoxyphenyl)-6-indolinyl-3H-benzo (f) chromene;
9) 3-(3-chloro-4-methoxyphenyl)-3-(3-methoxycarbonyl-4-isopropoxyphenyl)-6-morpholino-3H-benzo (f) chromene;
10) 3-(3-cyano-4-methoxyphenyl)-3-(4-methoxyphenyl)-6-morpholino-3H-benzo (f) chromene;
11) 3-(3-chloro-4-phenoxyphenyl)-3-(3-fluoro-4-methoxyphenyl)-6-(4-N-methylpiperadinyl)-3H-benzo (f) chromene;
12) 3,3-bis(3-fluoro-4-methoxyphenyl)-6-thiomorpholino-3H-benzo (f) chromene.

The numerals attached to the above-mentioned chromene compounds correspond to the compound numbers of Examples 1 to 12.

The chromene compound of the present invention usually exists in the form of a colorless or pale yellow solid or a viscous liquid at normal temperature under normal pressure, and can be confirmed by means (a) to (c) described below.

(a) Measurement of the proton nuclear magnetic resonance spectrum ($^1$H-NMR) indicates peaks near δ6.0 to 9.0 ppm due to aromatic proton and proton of alkene, and peaks near δ0.8 to 5.0 ppm due to protons of alkyl group and alkylene group. Upon relatively comparing the spectral intensities, furthermore, it is possible to know the number of protons of the bonded groups.

(b) The composition of a corresponding product can be determined based on the elemental analysis.

(c) Measurement of the $^{13}$C-nuclear magnetic resonance spectrum ($^{13}$C-NMR) indicates a peak near δ110 to 160 ppm based on carbon of aromatic hydrocarbon group, a peak near δ80 to 140 ppm due to carbon of alkene, and peaks near δ20 to 80 ppm due to carbon of alkyl group and alkylene group.

The chromene compound of the present invention can be produced by any method without any particular limitation. A representative method that is generally preferably employed comprises reacting a naphthol derivative represented by the following general formula (4),

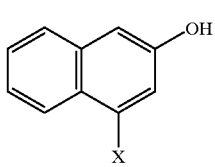

(4)

wherein X is as defined in the general formula (1), with a propargyl alcohol represented by the following general formula (5),

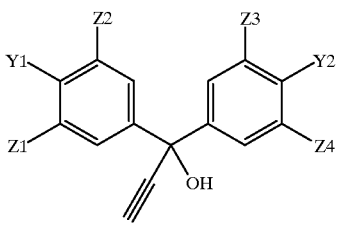

(5)

wherein Y1, Y2, Z1, Z2, Z3 and Z4 are as defined in the general formula (1),
in the presence of an acid catalyst.

There is no particular limitation on the methods of synthesizing the compounds represented by the above-mentioned general formulas (4) and (5), and these compounds can be synthesized by, for example, a method disclosed in WO9422850. That is, the naphthol derivative represented by the above-mention d general formula (4) can be synthesized by, for example, reacting a 2-naphthol with chlorine to form a 1,1-dichloro-2-naphthalenone which is then reacted with a secondary or primary amine corresponding to the substituent X in the above-mentioned general formula (1) in the presence of a base such as triethylamine to synthesize a 1-chloro-2-naphthol derivative, followed by the reaction with a reducing agent such as Raney nickel or the like. In this case, when a 2-naphthol is used having substituents at the third position, fifth position, sixth position, seventh position and eighth position, there can be synthesized a chromene compound having substituents at the fifth position, seventh position, eighth position, ninth position and tenth position of the naphthopyran ring. Furthermore, the propargyl alcohol derivative represented by the above-mentioned general formula (5) can be synthesized by, for example, reacting a benzophenone derivative having a substituent corresponding to the above-mentioned general formula (5) with a metal acetylene compound such as lithium acetylide.

The reaction of the compound represented by the above-mentioned general formula (4) with the compound represented by the above-mentioned general formula (5) is usually carried out as described below. That is, the reaction ratio of these two kinds of compounds is selected from a wide range, but is generally selected from a range of 1:10 to 10:1 (molar ratio). As the acid catalyst, furthermore, there is used sulfuric acid, benzenesulfonic acid, p-toluenesulfonic acid or acidic alumina in an amount of from 0.01 to 20 parts by weight with respect to the sum of the compounds (reaction substrates) represented by the above-mentioned general formulas (4) and (5). The reaction temperature is, usually, from 0 to 200° C. As the reaction solvent, there is used a non-protonic organic solvent such as N-methylpyrrolidone, dimethylformamide, tetrahydrofuran, benzene or toluene. The obtained reaction mixture is, as required, subjected to an ordinary treatments such as filtering, neutralization, extraction, washing with water, drying and condensation to obtain a solid or oily coarse object product.

As required, the obtained coarse product is refined based upon the washing with a poor solvent, recrystallization, column chromatography or treatment with an adsorbing agent.

The solvent used for the washing or recrystallization is selected, generally, from alcohols such as methanol, ethanol and isopropyl alcohol; ethers such as diethyl ether, diisopropyl ether, and tetrahydrofuran; esters such as methyl acetate, ethyl acetate and propyl acetate; aliphatic hydrocarbons such as pentane, hexane and heptane; aromatic hydrocarbons such as benzene, toluene and xylene; aliphatic halogenated hydrocarbons such as dichloromethane, chloroform and carbon tetrachloride; aromatic halogenated hydrocarbons such as chlorobenzene; carbonates such as dimethyl carbonate and diethyl carbonate; ketones such as acetone and methyl ethyl ketone; nitriles such as acetonitrile; and amides such as dimethylformamide and N-methylpyrrolidone. These solvents may be used in a single kind or, as required, being mixed together in two or more kinds at any ratio. The solvent is usually used in an amount of from 5 to 300 parts by weight with respect to the coarse object product. The solvent is used usually at a temperature of from −20 to 200° C. The temperature may be varied within the above-mentioned range in order to improve efficiency for removing impurities.

The carrier used for the column chromatography is generally silica gel, or acidic, neutral or basic alumina, or activated carbon. The amount of use is over a range of from 5 to 300 parts by weight with respect to the coarse object product. The mobile phase is generally selected from the above-mentioned range of solvents. The mobile phase may comprise a single solvent or a mixture of two or more kinds of solvents at any ratio.

The adsorbing agent is generally activated carbon, silica gel, or acidic, neutral or basic alumina, ion-exchange resin, zeolite, diatomaceous earth or montmorillonite. The amount of use is usually over a range of from 0.01 to 10 parts by weight with respect to the coarse product. In order to efficiently carry out the treatment with the adsorbing agent, the solvent is used in an amount larger than the amount of a solvent selected out of the above-mentioned solvents for dissolving the coarse product. Usually, the solvent is used in an amount over a range of from 5 to 300 parts by weight with respect to the coarse product though the amount may vary depending upon the dissolving power of the solvent. The treatment with the adsorbing agent is usually selected from a range of 0 to 100° C.

When the chromene compound of the present invention represented by the above-mentioned general formula (1) is dissolved in a general organic solvent such as toluene, chloroform or tetrahydrofuran, the solution is generally nearly colorless and transparent or is slightly colored. When irradiated with sunlight or ultraviolet rays, however, the solution readily develops color and returns back to its initial colorless state when light is shut off; i.e., the solution exhibits a favorable and reversible photochromic action.

The chromene compound of the present invention exhibits a similar favorable photochromic action even in a polymer matrix. The polymer matrix will be the one in which the chromene compound of the present invention homogeneously disperses. Examples of the polymer matrix that can be favorably used from an optical point of view include:

(i) thermoplastic resins such as polymethyl acrylate, polyethyl acrylate, polymethyl methacrylate, polyethyl methacrylate, polystyrene, polyacrylonitrile, polyvinyl alcohol, polyacrylamide, poly(2-hydroxyethylmethacrylate), polydimethylsiloxane and polycarbonate;

(ii) multivalent acrylic acid ester and multi-valent methacrylic acid ester compounds such as ethylene glycol diacrylate, diethylene glycol dimethacrylate, triethylene glycol dimethacrylate, tetraethylene glycol dimethacrylate, ethylene glycol bisglycidylmethacrylate, bisphenol A dimethacrylate, 2,2-bis(4-methacryloyloxyethoxyphenyl) propane, 2,2-bis(3,5- dibromo-4-methacryloyloxyethoxyphenyl) propane; multi-valent allyl compounds such as diallyl phthalate, diallyl terephthalate, diallyl isophthalate, diallyl tartrate, diallyl epoxysuccinate, diallyl fumarate, diallyl hexaphthalate, diallyl carbonate, allyl diglycol carbonate, and trimethylolpropanetriallyl carbonate; multi-valent thioacrylic acid and multi-valent thiomethacrylic acid ester compounds such as 1,2-bis(methacryloylthio) ethane, bis(2-acryloylthioethylsulfide), and 1,4-bis (methacryloylthiomethyl) benzene; acrylic acid ester compounds and methacrylic acid ester compounds such as glycidyl acrylate, glycidyl methacrylate, β-methylglycidyl methacrylate, 3-(glycidyl-2-oxyethoxy)-2-hydroxypropyl methacrylate, 3-(glycidyloxyethoxy)-2-hydroxypropyl methacrylate, 3-(glycidyloxy-2-propyloxy)-2-hydroxypropyl acrylate; polymers of a radically polymerizable polyfunctional monomer such as divinyl benzene; and (iii) copolymers of the monomers (ii) and radically polymerizable monofunctional monomers like unsaturated carboxylic acids such as acrylic acid, methacrylic acid and maleic anhydride; acrylic acid and methacrylic acid ester compounds such as methyl acrylate, methyl methacrylate, benzyl methacrylate, phenyl methacrylate and 2-hydroxyethyl methacrylate; fumaric ester compounds such as diethyl fumarate and diphenyl fumarate; thioacrylic acid and thiomethacrylic acid ester compounds such as methylthio acrylate, benzylthio acrylate and benzylthio methacrylate; and vinyl compounds such as styrene, chlorostyrene, methylstyrene, vinylnaphthalene, α-methylstyrene dimer, and bromostyrene.

The chromene compound of the present invention can be dispersed in the polymer matrix by a general method without any particular limitation. Examples include a method in which the thermoplastic resin and the chromene compound of the invention are kneaded together in a molten state and are dispersed in the resin, a method in which the chromene compound of the invention is dissolved in the polymerizable monomer followed by the addition of a polymerization catalyst, and is polymerized with heat or light and is dispersed in the resin, or a method in which the chromene compound of the invention is dyed on the surfaces of the thermoplastic resin and the thermosetting resin so as to be dispersed in the resins.

The chromene compound of the present invention can be extensively used as a photochromic material, for example, as a variety of memory materials like a variety kinds of photosensitive materials, copying materials, photosensitive materials for printing, memory material for cathode-ray tubes, photosensitive material for lasers, and photosensitive material for holography, to substitute silver salt photosensitive materials. Moreover, the photochromic material using the chromene compound of the present invention can be used as a material of photochromic lens, material of optical filter, material of display, as an actinometer and as an ornamental material.

When used for a photochromic lens, for example, there is no particular limitation provided there is obtained a homogeneously dimming material. Concrete examples include a method in which a polymer film containing the photochromic material of the present invention homogeneously dispersed therein is sandwiched in a lens, a method in which the chromene compound of the invention is dispersed in the polymerizable monomer and is polymerized according to a predetermined method, and a method in which the compound is dissolved in, for example, a silicone oil and with which the surfaces of the lens is impregnated at 150 to 200° C. over 10 to 60 minutes, and the surfaces are coated with a curing material to obtain a photochromic lens. Furthermore, a method can be contrived to coat the surfaces of the lens with the polymer film to coat the surfaces of a curable substance in order to obtain a photochromic lens.

An ultraviolet ray-absorbing agent may be added to the photochromic lens in order to improve light resistance. As the ultraviolet ray-absorbing agent, there can be used, without any limitation, any known ultraviolet ray absorbing agent that has been added to a variety of plastics. Examples of the ultraviolet ray absorbing agent that can be favorably used in the present invention include benzotriazole-type ultraviolet-ray absorbing agent, benzophenone-type ultraviolet ray absorbing agent, salicylic acid-type ultraviolet-ray absorbing agent and cyanoacrylate-type ultraviolet ray absorbing agent.

Among the ultraviolet ray absorbing agents, the benzotriazole-type ultraviolet ray absorbing agent is particularly effective in improving the light resistance. As the benzo-triazole-type ultraviolet ray absorbing agent, a known compound having a benzotriazole skeleton and ultraviolet ray-absorbing function can be used without any limitation. For example, the benzotriazole-type ultraviolet ray absorbing agent represented by the following general formula (6) can be preferably used,

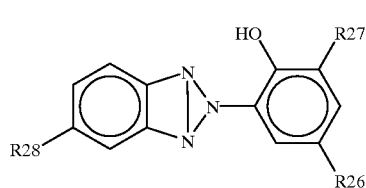

(6)

wherein R26 and R27 may be the same or different and are hydrogen atoms, alkyl groups, aryl groups or aralkyl groups, and R28 is a hydrogen atom or a chlorine atom.

In the above-mentioned general formula (6), the alkyl groups represented by R26 and R27 may be those having 1 to 10 carbon atoms, such as methyl groups, butyl groups, sec-butyl groups or t-butyl groups. The aryl group may be the one having 6 to 20 carbon atoms, such as phenyl group, butylphenyl group, sec-butylphenyl group or t-butylphenyl group. The aralkyl group may be the one having 7 to 20 carbon atoms, such as benzyl group or phenylethyl group.

A compound that can be suitably used as the benzotriazole-type ultraviolet ray absorbing agent is the one in which R26 and R27 in the general formula (6) are the same or different, and are alkyl groups having 1 to 5 carbon atoms and, particularly, methyl groups, t-butyl groups, amyl groups, aryl groups having 6 to 15 carbon atoms and, particularly, methylphenyl groups, t-butylphenyl groups, t-octylphenyl groups, or aralkyl groups having 7 to 15 carbon atoms and, particularly, benzyl groups, or α,α-dimethylbenzyl groups.

Concrete examples of the benzotriazole-type ultraviolet ray absorbing agent that can be favorably used in the present invention include the following compounds:

(1) 2-(5-methyl-2-hydroxyphenyl) benzotriazole [trade name: TINUVIN P, manufactured by Nippon CIBA GEIGY Co.]
(2) 2-[2-hydroxy-3,5-bis(α,α-dimethylbenzyl) phenyl]-2H-benzotriazole [trade name: TINUVIN 234, manufactured by Nippon CIBA GEIGY Co.]
(3) 2-(3,5-di-t-butyl-2-hydroxyphenyl) benzotriazole [trade name: TINUVIN 320, manufactured by Nippon CIBA GEIGY Co.]

(4) 2-(3-t-butyl-5-methyl-2-hydroxyphenyl)-5-chlorobenzotriazole [trade name: TINUVIN 326, manufactured by Nippon CIBA GEIGY Co.]

(5) 2-(3,5-di-t-butyl-2-hydroxyphenyl)-5-chlorobenzotriazole [trade name: TINUVIN 327, manufactured by Nippon CIBA GEIGY Co.]

(6) 2-(3,5-di-t-amyl-2-hydroxyphenyl) benzotriazole [trade name: TINUVIN 328, manufactured by Nippon CIBA GEIGY Co.]

(7) 2-(2'-hydroxy-5'-t-octylphenyl) benzotriazole [trade name: TINUVIN 329, manufactured by Nippon CIBA GEIGY Co.]

The numerals attached to the above-mentioned benzotriazole-type ultraviolet ray absorbing agents correspond to the ultraviolet ray-absorbing agent numbers of Examples 25 to 30.

The ultraviolet ray absorbing agents are blended in amounts of from 1 to 10000 parts by weight and, preferably, from 5 to 5000 parts by weight per 100 parts by weight of the chromene compound.

The chromene compound of the present invention develops a color of a high density in a solution or in a polymer matrix, permits the color to fade quickly, and is initially colored little. For example, the photochromic lens using the chromene compound of the present invention is initially colored little before it develops color, develops a color to exhibit excellent light-shielding property upon irradiation with sunlight or ultraviolet rays, and quickly returns to the initial state after it is no longer irradiated with light.

EXAMPLES

The present invention will be described in further detail by way of Examples to which only, however, the invention is in no way limited.

Example 1

2.29 Grams of a compound of the following formula (7),

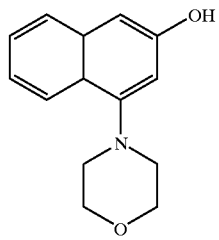

(7)

and 3.72 g of a compound of the following formula (8),

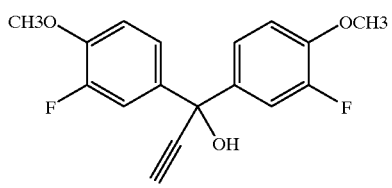

(8)

were dissolved in 60 ml of toluene, followed by the addition of 23 g of acidic alumina, and the mixture was refluxed for 2 hours. After the reaction, alumina was filtered, the solvent was distilled off, and a mixture solvent of hexane/ethyl acetate=2/1 was subjected to the chromatography on a silica gel that was used for the mobile phase. After condensing the solvent. recrystallization was conducted by using toluene and isopropyl alcohol to obtain 2.60 g of a pale yellow powdery product.

Elemental analysis of the product showed C72.18%, H5.30%, F7.40%, N2.76%, and O12.36%, which were in very good agreement with C72.22%, H5.28%, F7.37%, N2.72% and O12.41% calculated from $C_{31}H_{27}F_2NO_4$.

Measurement of the proton nuclear magnetic resonance spectrum showed peaks 13H near δ6.0 to 9.0 ppm due to aromatic proton and proton of alkene, and peaks 14H near δ3.0 to 4.0 ppm due to alkoxy group and morpholino group as shown in FIG. 1.

Moreover, measurement of the $^{13}$C-nuclear magnetic resonance spectrum showed a peak near δ110 to 160 ppm due to carbon of an aromatic ring, and a peak near δ80 to 140 ppm due to carbon of alkene.

From the above results, it was confirmed that the isolated product was a compound represented by the following structural formula. Hereinafter, this compound is referred to as compound No. 1.

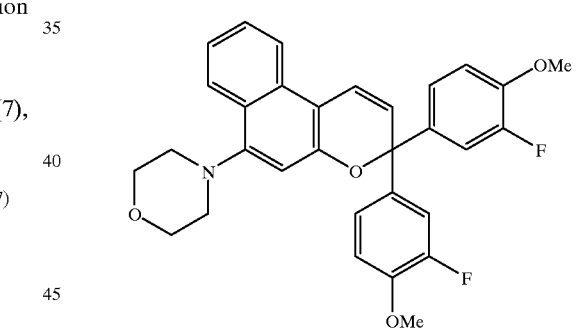

Examples 2 to 12

The chromene compounds were synthesized by using starting materials shown in Table 2 in the same manner as in Example 1. The structures of the obtained products were analyzed by using the same identification method (or characterization method) as that of Example 1, and it was confirmed that the compounds were those having structural formulas shown in Table 2. Table 3 shows values of elemental analysis of these compounds, values calculated from the structural formulas of these compounds, and characteristic spectra of $^1$H-NMR spectra. The compounds obtained in Examples 2 to 12 are hereinafter referred to as compounds Nos. 2 to 12.

TABLE 2

| Ex. | Starting material | Starting material | Product | Yield (%) |
|---|---|---|---|---|
| 2 | (structure) | (structure) | (structure) | 45 |
| 3 | (structure) | (structure) | (structure) | 22 |
| 4 | (structure) | (structure) | (structure) | 25 |

TABLE 2-continued

| Ex. | Starting material | Product | Yield (%) |
|---|---|---|---|
| 5 | | | 28 |
| 6 | | | 35 |
| 7 | | | 44 |

TABLE 2-continued

| Ex. | Starting material | Product | Yield (%) |
|---|---|---|---|
| 8 | | | 15 |
| 9 | | | 12 |
| 10 | | | 9 |

TABLE 2-continued

| Ex. | Starting material | Product | Yield (%) |
|---|---|---|---|
| 11 | | | 16 |
| 12 | | | 46 |

TABLE 3

| Example | Found C | Found H | Found N | Found O | Found Others | Calculated C | Calculated H | Calculated N | Calculated O | Calculated Others | 1H-NMR spectrum (ppm) |
|---|---|---|---|---|---|---|---|---|---|---|---|
| 2 | 72.30 | 5.31 | 2.80 | 12.26 | F:7.33 | 72.22 | 5.28 | 2.72 | 12.41 | F: 7.37 | δ 6.0~9.0(13H)<br>δ 3.0~4.0(14H) |
| 3 | 76.95 | 5.19 | 2.55 | 8.64 | F:6.67 | 76.99 | 5.20 | 2.49 | 8.55 | F: 6.77 | δ 6.0~9.0(17H)<br>δ 3.0~4.0(7H)<br>δ 1.6~2.5(5H) |
| 4 | 79.80 | 5.80 | 2.55 | 8.55 | F:3.30 | 79.69 | 5.78 | 2.51 | 8.61 | F: 3.41 | δ 6.0~9.0(18H)<br>δ 3.0~4.0(10H)<br>δ 1.6~2.5(4H) |
| 5 | 79.45 | 5.55 | 2.63 | 5.77 | Cl:6.60 | 79.47 | 5.56 | 2.57 | 5.88 | Cl: 6.52 | δ 6.0~9.0(18H)<br>δ 3.0~4.0(5H)<br>δ 1.6~2.5(7H) |
| 6 | 68.72 | 5.44 | 2.46 | 14.08 | Cl:6.05<br>F:3.25 | 68.81 | 5.42 | 2.43 | 13.89 | Cl: 6.15<br>F: 3.30 | δ 6.0~9.0(13H)<br>δ 3.0~4.0(18H) |
| 7 | 61.10 | 4.44 | 2.33 | 7.86 | Br:13.18<br>Cl:5.75<br>S:5.34 | 61.14 | 4.47 | 2.30 | 7.88 | Br: 13.12<br>Cl: 5.82<br>S: 5.27 | δ 6.0~9.0(13H)<br>δ 3.0~4.0(14H) |
| 8 | 75.30 | 5.48 | 2.30 | 7.84 | F:9.08 | 75.35 | 5.51 | 2.25 | 7.72 | F: 9.17 | δ 6.0~9.0(18H)<br>δ 3.0~4.0(5H)<br>δ 1.4~2.5(11H) |
| 9 | 69.95 | 5.68 | 2.41 | 16.19 | Cl:5.77 | 70.05 | 5.71 | 2.33 | 16.00 | Cl: 5.91 | δ 6.0~9.0(13H)<br>δ 3.0~4.0(15H)<br>δ 1.6~2.0(6H) |
| 10 | 76.08 | 5.55 | 5.50 | 12.79 |  | 76.17 | 5.59 | 5.55 | 12.68 |  | δ 6.0~9.0(14H)<br>δ 3.0~4.0(16H) |
| 11 | 73.15 | 5.31 | 4.54 | 8.05 | Cl:5.92<br>F:3.03 | 73.20 | 5.31 | 4.61 | 7.91 | Cl: 5.84<br>F: 3.13 | δ 6.0~9.0(18H)<br>δ 3.0~4.0(14H) |
| 12 | 70.00 | 5.15 | 2.75 | 8.88 | F:7.02<br>S:6.20 | 70.04 | 5.12 | 2.63 | 9.03 | F: 7.15<br>S: 6.03 | δ 6.0~9.0(13H)<br>δ 3.0~4.0(14H) |

Examples 13 to 24, Comparative Examples 1 to 3

0.05 Parts of the chromene compound obtained in Example 1 was added to 70 parts of a tetraethylene glycol dimethacrylate, 15 parts of a triethylene glycol dimethacrylate, 10 parts of a glycidyl methacrylate and 5 parts of a 2-hydroxyethyl methacrylate, and was mixed together to a sufficient degree. The mixture solution was poured into a mold constituted by a glass plate and a gasket of an ethylene/vinyl acetate copolymer, and was cast-polymerized. By using an air furnace, the polymerization was conducted in a manner that the temperature was gradually raised from 30° C. to 90° C. over a period of 18 hours, and was held at 90° C. for 2 hours. After the polymerization, the polymer was taken out from the glass mold.

By using a xenon lamp, L-2480(300W)SHL-100, manufactured by Hamamatsu Photonics Co., the obtained polymer (2 mm thick) was irradiated with a beam of an intensity of 365 nm=2.4 mW/cm$^2$ and 245 nm=24 µW/cm$^2$ on the surface of the polymer for 120 seconds through an aero-mass filter (manufactured by Corning Co.) at 20° C.±1° C. to develop color and to measure the photochromic properties which were expressed in the following manner. Maximum absorption wavelength (λmax: unit in nm): λmax of the polymer after it has developed color was found by using a spectrophotometer (instantaneous multi-channel photodetector, MCPD1000) manufactured by OTSUKA ELECTRONICS CO. LTD.

ε(120): Absorbency of the polymer at a maximum absorption wavelength after it was irradiated for 120 seconds under the above-mentioned conditions.

ε(0): Absorbency of the polymer in a non-irradiated state at a wavelength same as the maximum absorption wavelength of when it is irradiated with light.

ε(120)–ε(0): Color density Color fading rate (τ½:unit in min.): Time required until the absorbency of the polymer drops down to one-half of [ε(120)–ε(0)] after irradiated for 120 seconds.

The results were as shown in Table 4. Moreover, photochromic polymers were obtained in the same manner as described above but using, as chromene compounds, the compounds obtained in Examples 2 to 12. Their properties were as shown in Table 4.

For the purpose of comparison, furthermore, Table 4 shows the properties of the chromene compounds represented by the following formulas (A), (B) and (C).

TABLE 4

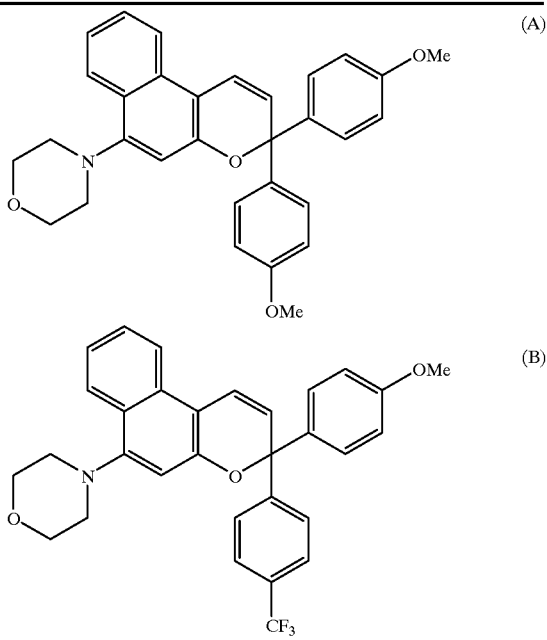

TABLE 4-continued (C)

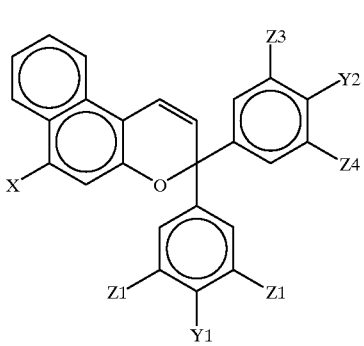

| Example | Compound No. | λMax (nm) | Initial color ε(0) | Color density ε(120)– ε(0) | Color fading rate τ½(min) |
|---|---|---|---|---|---|
| 13 | 1 | 442 | 0.05 | 1.13 | 4.0 |
| 14 | 2 | 446 | 0.05 | 1.08 | 3.8 |
| 15 | 3 | 460 | 0.02 | 0.92 | 3.0 |
| 16 | 4 | 470 | 0.01 | 1.07 | 3.5 |
| 17 | 5 | 468 | 0.01 | 1.00 | 3.3 |
| 18 | 6 | 444 | 0.05 | 1.18 | 4.2 |
| 19 | 7 | 440 | 0.04 | 1.20 | 4.5 |
| 20 | 8 | 460 | 0.02 | 1.05 | 3.0 |
| 21 | 9 | 440 | 0.04 | 1.20 | 4.2 |
| 22 | 10 | 440 | 0.04 | 1.16 | 4.5 |
| 23 | 11 | 448 | 0.04 | 1.20 | 4.3 |
| 24 | 12 | 444 | 0.05 | 1.10 | 3.8 |
| Comp.Ex. | | | | | |
| 1 | A | 456 | 0.11 | 1.08 | 3.8 |
| 2 | B | 432 | 0.06 | 1.20 | 9.6 |
| 3 | C | 430 | 0.20 | 1.52 | >10 |

The compounds of the present invention has initial colors that are not more than one-half that of the compound (A) of Comparative Example 1. Compared to the compound (B) of Comparative Example 2 and the compound (C) of Comparative Example 3, furthermore, the compounds of the present invention exhibit nearly the same initial colors but permit the color to fade at a rate of more than two times as large.

Example 25

A photochromic polymer was obtained in the same manner as in Example 13 but adding 0.05 parts by weight of TINUVIN P as an ultraviolet ray absorbing agent with respect to 0.05 parts by weight of the chromene compound of the present invention (that is, 0.05 parts by weight of TINUVIN P per 100 parts by weight of the monomer mixture).

The obtained polymer was evaluated for its light resistance.

That is, by using a color difference meter manufactured by Suga Shikenki Co., the photochromic polymer of before being used was measured for its yellowness index (YI). Then, the photochromic polymer was irradiated with sunlight for 30 minutes to develop color, and its color was permitted to fade for one hour in the light of a fluorescent lamp. This cycle was repeated three times a day for a total of 30 days. The photochromic polymer after tested was measured for its Y1 in the same manner as before it was used. Based upon these measurements, light resistance of the photochromic polymer was found as defined below.

Light resistance (ΔYI)=YI of the polymer after used −YI of the polymer before used.

The result was as shown in Table 5.

Examples 26 to 30

The procedure was repeated in the same manner as in Example 25 but changing the chromene compound and the ultraviolet ray absorbing agent. The results were as shown in Table 5.

Comparative Examples 1 and 2

The procedure was conducted in the same manner as in Example 25 by using the chromene compound of the present invention and a known chromene compound but without using ultraviolet ray absorbing agent. The results were as shown in Table 5.

From the results of Table 5, it will be understood that the light resistance is improved by the addition of the ultraviolet ray absorbing agent.

TABLE 5

| | Chromene compound | | Ultraviolet ray absorbing agent | | |
|---|---|---|---|---|---|
| Example | No. | Added amount (pts. by wt.) | No. | Added amount (ptd. by wt.) | ΔYI |
| 25 | 1 | 0.05 | 1 | 0.05 | 2.2 |
| 26 | 1 | 0.05 | 1 | 0.02 | 2.6 |
| 27 | 1 | 0.02 | 1 | 0.05 | 1.7 |
| 28 | 2 | 0.05 | 7 | 0.05 | 2.3 |
| 29 | 4 | 0.05 | 1 | 0.05 | 2.3 |
| 30 | 12 | 0.05 | 4 | 0.05 | 2.1 |
| Comp. Ex. | | | | | |
| 1 | 1 | 0.05 | — | — | 4.5 |
| 2 | A | 0.05 | — | — | 6.1 |

We claim:

1. A photochromic lens containing a chromene compound represented by the following general formula (1)

(1)

wherein X is an amino group represented by the following formula (2),

—NR1R2 (2)

wherein R1 and R2 may be the same or different, and are hydrogen atoms, substituted or unsubstituted alkyl groups having 1 to 10 carbon atoms, substituted or unsubstituted aryl groups or hetero rings, having 6 to 10 carbon atoms, or a cyclic amino group represented by the following formula (3),

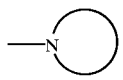

wherein the ring may contain a hetero atom, or may contain a hetero ring and/or an aromatic ring in a condensed form, Y1 and Y2 may be the the same or different and are electron-donating groups, Z1, Z2, Z3 and Z4 may be the same or different and are hydrogen atoms or electron-attracting groups, at least one of Z1 to Z4 is an electron-attracting group, and a carbon atom at any one of fifth position, seventh position, eighth position, ninth position or tenth position of a naphthopyran ring may have a substituent.

2. The photochromic lens according to claim 1 further comprising from 1 to 10,000 parts by weight of an ultraviolet ray absorbing agent per 100 parts by weight of said chromene compound.

3. The photochromic lens according to claim 1, wherein said lens comprises a thermoplastic resin polymer matrix.

4. The photochromic lens according to claim 3 wherein said thermoplastic resin comprises a polymer selected from the group consisting of polymethyl acrylate, polyethyl acrylate, polymethyl methacrylate, polyethyl methacrylate, polystyrene, polyacrylonitrile, polyvinyl alcohol, polyacrylamide, poly(2-hydroxyethylmethacrylate), polydimethylsiloxane and polycarbonate.

5. The photochromic lens according to claim 1, wherein said lens comprises a polymer matrix comprising polymer of a radically polymerizable polyfunctional monomer.

6. The photochromic lens according to claim 5, wherein said radically polymerizable polyfunctional monomer is at least one compound selected from the group consisting of polyfunctional acrylic acid ester compounds, polyfunctional methacrylic acid ester compounds, polyfunctional allyl compounds, polyfunctional thioacrylic acid ester compounds, polyfunctional thiomethacrylic acid ester compounds, polyfunctional glycidyl-containing esters of acrylic acid, polyfunctional glycidyl-containing esters of methacrylic acid, and divinyl benzene.

7. The photochromic lens according to claim 6, wherein the polyfunctional monomer is at least one compound selected from the group consisting of ethylene glycol diacrylate, diethylene glycol dimethacrylate, triethylene glycol dimethacrylate, tetraethylene glycol dimethacrylate, ethylene glycol bisglycidylmethacrylate, bisphenol A dimethacrylate, 2,2-bis(4-methacryloyloxyethoxyphenyl) propane, 2,2-bis(3,5-dibromo-4-methacryloyloxyethoxyphenyl) propane, diallyl phthalate, diallyl terephthalate, diallyl isophthalate, diallyl tartrate, diallyl epoxysuccinate, diallyl fumarate, diallyl hexaphthalate, diallyl carbonate, allyl diglycol carbonate, trimethylolpropanetriallyl carbonate, 1,2-bis (methacryloylthio) ethane, bis(2-acryloylthioethylsulfide), 1,4-bis(methacryloylthiomethyl) benzene, glycidyl acrylate, glycidyl methacrylate, β-methylglycidyl methacrylate, 3-(glycidyl-2-oxyethoxy)-2-hydroxypropyl methacrylate, 3-(glycidyloxyethoxy)-2-hydroxypropyl methacrylate, 3-(glycidyloxy-2-propyloxy)-2-hydroxypropyl acrylate, and divinyl benzene.

8. The photochromic lens according to claim 1, wherein said lens comprises a polymer matrix comprising copolymer of radically polymerizable polyfunctional monomer and radically polymerizable monofunctional monomer.

9. The photochromic lens according to claim 8, wherein said radically polymerizable polyfunctional monomer is at least one compound selected from the group consisting of polyfunctional acrylic acid ester compounds, polyfunctional methacrylic acid ester compounds, polyfunctional allyl compounds, polyfunctional thioacrylic acid ester compounds, polyfunctional thiomethacrylic acid ester compounds, polyfunctional glycidyl esters of acrylic acid, polyfunctional glycidyl esters of methacrylic acid, and divinyl benzene.

10. The photochromic lens according to claim 8, wherein the polyfunctional monomer is at least one compound selected from the group consisting of ethylene glycol diacrylate, diethylene glycol dimethacrylate, triethylene glycol dimethacrylate, tetraethylene glycol dimethacrylate, ethylene glycol bisglycidylmethacrylate, bisphenol A dimethacrylate, 2,2-bis(4-methacryloxyethoxyphenyl) propane, 2,2-bis(3,5-dibromo-4-methacryloyloxyethoxyphenyl) propane, diallyl phthalate, diallyl terephthalate, diallyl isophthalate, diallyl tartrate, diallyl epoxysuccinate, diallyl fumarate, diallyl hexaphthalate, diallyl carbonate, allyl diglycol carbonate, trimethylolpropanetriallyl carbonate, 1,2-bis (methacryloylthio) ethane, bis(2-acryloylthioethylsulfide), 1,4-bis(methacryloylthiomethyl) benzene, glycidyl acrylate, glycidyl methacrylate, β-methylglycidyl methacrylate, 3-(glycidyl-2-oxyethoxy)-2-hydroxypropyl methacrylate, 3-(glycidyloxyethoxy)-2-hydroxypropyl methacrylate, 3-(glycidyloxy-2-propyloxy)-2-hydroxypropyl acrylate, and divinyl benzene.

11. The photochromic lens according to claim 8, wherein said radically polymerizable monofunctional monomer is at least one compound selected from the group consisting of monofunctional unsaturated carboxylic acids, monofunctional acrylic acid ester compounds, monofunctional methacrylic acid ester compounds, monofunctional fumaric acid ester compounds, monofunctional thioacrylic acid ester compounds, monofunctional thiomethacrylic acid ester compounds, and monofunctional vinyl compounds.

12. The photochromic lens according to claim 11, wherein the monofunctional monomer is at least one compound selected from the group consisting of acrylic acid, methacrylic acid, maleic anhydride, methyl acrylate, methyl methacrylate, benzyl methacrylate, phenyl methacrylate, 2-hydroxyethyl methacrylate, diethyl fumarate, diphenyl fumarate, methylthio acrylate, benzylthio acrylate, benzylthio methacrylate, styrene, chlorostyrene, methylstyrene, vinylnaphthalene, α-methylstyrene dimer and bromostyrene.

13. The photochromic lens according to claim 1 which comprises a polymer matrix formed by polymerizing a polymerizable monomer in the presence of said chromene compound.

14. The photochromic lens according to claim 1 which comprises a lens at least one surface of which is impregnated with said chromene compound.

15. The photochromic lens according to claim 1 wherein the chromene compound is selected from the group consisting of 3,3-bis(3-fluoro-4-methoxyphenyl)-6-morpholino-3H-benzo (f) chromene, 3-(3,5-difluoro-4-methoxyphenyl)-3-(4-methoxyphenyl)-6-morpholine-3H-benzo (f) chromene, 3,3-bis(3-fluoro-4-methoxyphenyl)-6-(2-methylindolinyl)-3H-benzo (f) chromene, 3-(3-fluoro-4-methoxyphenyl)-3-(4-methoxymethylphenyl)-6-tetrahydroquinolinyl)-3H-benzo (f) chromene, 3-(3-chloro-4-methylphenyl)-3-(4-methoxyphenyl)-6-(tetrahydroquinolinyl)-3H-benzo (f) chromene, 3-(3-chloro-4-(2-methoxyethoxy)phenyl)-3-(3-fluoro-4-methoxyphenyl)-6-morpholino-3H-benzo (f) chromene, 3-(3-bromo-4-methoxyphenyl)-3-(3-chloro-4-methoxyphenyl-6-thiomorpholino-3H-benzo (f) chromene, 3-(4-t-butoxyphenyl)-3-(3-trifluoromethyl-4-methoxyphenyl)-6-indolinyl-3H-benzo (f) chromene, 3-(3-chloro-4-methoxyphenyl)-3-(3-methoxycarbonyl-4-isopropoxyphenyl)-6-morpholino-3H-benzo (f) chromene, 3-(3-cyano-4-methoxyphenyl)-3-(4-methoxyphenyl)-6-morpholino-3H-benzo (f) chromene, 3-(3-chloro-4-phenoxyphenyl)-3-(3-fluoro-4-methoxyphenyl)-6-(4-N-methylpiperadinyl)-3H-benzo (f) chromene, and 3,3-bis(3-fluoro-4-methoxyphenyl)-6-thiomorpholino-3H-benzo (f) chromene.

16. The photochromic lens according to claim 2 wherein the ultraviolet ray absorbing agent is present in an amount of from 5 to 5000 parts per 100 parts of the chromene compound.

17. The photochromic lens according to claim 2 wherein the ultraviolet ray absorbing agent is a benzo-triazole containing compound.

* * * * *